(12) United States Patent
Lee et al.

(10) Patent No.: US 12,370,307 B2
(45) Date of Patent: Jul. 29, 2025

(54) USE OF FUZZY LOGIC IN PREDICTING USER BEHAVIOR AFFECTING BLOOD GLUCOSE CONCENTRATION IN A CLOSED LOOP CONTROL SYSTEM OF AN AUTOMATED INSULIN DELIVERY DEVICE

(71) Applicant: Insulet Corporation, Acton, MA (US)

(72) Inventors: Joon Bok Lee, Acton, MA (US);
Ashutosh Zade, San Diego, CA (US);
Jason O'Connor, Acton, MA (US);
Yibin Zheng, Hartland, WI (US);
Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 1089 days.

(21) Appl. No.: 17/166,072

(22) Filed: Feb. 3, 2021

(65) Prior Publication Data

US 2021/0236730 A1     Aug. 5, 2021

Related U.S. Application Data

(60) Provisional application No. 62/969,393, filed on Feb. 3, 2020.

(51) Int. Cl.
*A61M 5/172*     (2006.01)
*G16H 10/60*     (2018.01)
(Continued)

(52) U.S. Cl.
CPC .......... *A61M 5/1723* (2013.01); *G16H 10/60* (2018.01); *G16H 20/17* (2018.01); *G16H 20/30* (2018.01);
(Continued)

(58) Field of Classification Search
CPC ............ A61B 5/14532; A61M 5/1723; A61M 2005/14208; A61M 2230/201; A61M 2205/52; G16H 20/17
See application file for complete search history.

(56) References Cited

U.S. PATENT DOCUMENTS 303,013 A     8/1884    Horton
2,797,149 A     6/1957    Skeggs
(Continued)

FOREIGN PATENT DOCUMENTS

AU     2015200834 A1     3/2015
AU     2015301146 A1     3/2017
(Continued)

OTHER PUBLICATIONS

US 5,954,699 A, 09/1999, Jost et al. (withdrawn)
(Continued)

*Primary Examiner* — Devin B Henson
(74) *Attorney, Agent, or Firm* — Goodwin Procter LLP

(57) ABSTRACT

In an automated insulin delivery device, fuzzy logic may be applied to the responding to the possibility of a user taking additional action that may affect the blood glucose concentration. Fuzzy sets may be defined for empirically derived different likelihoods of the user taking such additional action based on correlated factors. A membership function may be provided for each fuzzy set. The membership function may provide a probability of membership in the set based on a parameter. Each fuzzy set may have a response that is reflective of the likelihood of additional user action associated with the fuzzy set. The responses by the AID device to each of these cases may reflect the probability of each such case occurring as evidenced by empirical data.

21 Claims, 13 Drawing Sheets

(51) Int. Cl.
*G16H 20/17* (2018.01)
*G16H 20/30* (2018.01)
*G16H 50/20* (2018.01)

(52) U.S. Cl.
CPC ....... *G16H 50/20* (2018.01); *A61M 2205/505* (2013.01); *A61M 2205/52* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute, deceased et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |

(56) References Cited

U.S. PATENT DOCUMENTS

| | | |
|---|---|---|
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,561,788 B2 * | 2/2020 | Roy .................... A61M 5/1723 |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 11,696,728 B2 * | 7/2023 | Patek .................... G16H 50/30 |
| | | 705/2 |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |

(56) References Cited

U.S. PATENT DOCUMENTS

| | | |
|---|---|---|
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |

(56) References Cited

U.S. PATENT DOCUMENTS

| | | |
|---|---|---|
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0273610 A1* | 9/2017 | Suri ............... A61B 5/15105 |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277246 A1* | 9/2018 | Zhong ............... A61B 5/746 |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |

(56) References Cited

FOREIGN PATENT DOCUMENTS

| | | |
|---|---|---|
| EP | 1571582 B1 | 4/2019 |
| EP | 2897071 B1 | 5/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 05110601 A1 | 5/2004 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

European Search Report for the European Patent Application No. 21168591.2, mailed Oct. 13, 2021, 04 pages.
International Search Report and Written Opinion for the International Patent Application No. PCT/US2021/041954, mailed Oct. 25, 2021, 13 pages.
International Search Report and Written Opinion for the International Patent Application No. PCT/US2021/047771, mailed Dec. 22, 2021, 11 pages.
International Search Report and Written Opinion for the International Patent Application No. PCT/US2021/052855, mailed Dec. 22, 2021, 11 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. ""Single-Versus Triple-Lumen Central Catheter-Related Sepsis: A Prospective Randomized Study in a Critically Ill Population"" The American Journal of Medicine September 1992vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination Of Haemodialysis Catheter Connections"" Journal of Renal Care,European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

(56) References Cited

OTHER PUBLICATIONS

Schlegel et al, "Multilumen Central Venous Catheters Increase Risk for Catheter-Related Bloodstream Infection: Prospective Surveillance Study".

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010 (OPTIS.247VPC).

International Search Report and Written Opinion in PCT/US2008/079641 (Optis.203VPC) dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (2008, July).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (2001, October).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agoritm for Blood Gucose Control in Type 1 Diabetic Patients." IEEE Transactions on Biomedical Engineering, 46 (2) 148-147 (1999).

(56) References Cited

OTHER PUBLICATIONS

International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030652, Sep. 25, 2019, 19 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/022694, mailed Jun. 25, 2021, 13 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (un. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G .; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.

\* cited by examiner

| Likelihood of Additional User Action | Intensity of User Activity | | | |
|---|---|---|---|---|
| Meal Size Relative to User's Standard | None (1212) | Low (1214) | Med (1216) | High (1218) |
| Low | Low | Low | Moderate | High |
| Normal | Low | Moderate | High | Very High |
| High | Moderate | High | Very High | Very High |

FIG. 12

USE OF FUZZY LOGIC IN PREDICTING USER BEHAVIOR AFFECTING BLOOD GLUCOSE CONCENTRATION IN A CLOSED LOOP CONTROL SYSTEM OF AN AUTOMATED INSULIN DELIVERY DEVICE

CROSS-REFERENCE TO RELATED APPLICATIONS

This application claims the benefit of the filing date of U.S. Provisional Application Ser. No. 62/969,393, filed Feb. 3, 2020, the entire contents of which are incorporated herein by reference in their entirety.

BACKGROUND

In automated insulin delivery (AID) device, insulin is delivered to a user automatically via a pumping mechanism under the control of a controller, such as a processor. The controller may implement a closed loop control approach where a glucose monitor provides current information regarding the glucose blood concentration of a user and the glucose blood concentration of the user is used to adjust the dosage of insulin delivered to the user. Typically, the AID device seeks to keep the blood glucose concentration of the user within a range or seeks to achieve a target blood glucose concentration.

One of the risks with treating a user with an AID device is hypoglycemia. The user may take actions that increase the risk of hypoglycemia. Examples of such user actions include but are not limited to taking too large of insulin boluses, taking too small of insulin boluses, overestimating the carbohydrate content of a meal, signaling a desire to have a correction bolus and not ingesting a meal, etc. Conventional AID systems do not adequately account for these user actions that increase the risk of hypoglycemia.

SUMMARY

In accordance with an exemplary embodiment, a method is performed by a processor for controlling an AID device. Per this method blood glucose history, insulin bolus history and/or meal event flags for a user of the AID device are analyzed to identify when the user has ingested meals and to categorize sizes of the ingested meals. The blood glucose history, insulin delivery history and/or user-entered information for the user are analyzed to identify when the user has exercised and categorizing an intensity of the identified user exercise. The blood glucose history for the user and the insulin delivery history for the user are analyzed to determine the likelihood that the user will take additional action affecting blood glucose over time of day based on when the meals are ingested, the categorized sizes of the meals ingested, when the user exercises and the categorized intensity of exercise of the user. Fuzzy sets are established for categories of the determined likelihoods that the user will take additional action affecting blood glucose. Each fuzzy set is associated with a quantitative response to be taken by the AID device according to the respective categories of determined likelihoods that the user will take additional action. For a given time of day, a set membership probability for the user is determined for each of the fuzzy sets based on the determined likelihood that the user will take additional action affecting blood glucose for the given time of day. The quantitative responses of each of the fuzzy sets are weighted by the determined membership probabilities for the respective fuzzy sets, and the weighted quantitative responses of the fuzzy sets are summed to determine the cumulative response to apply. The cumulative response is applied in the AID device.

The identifying of when the user has ingested meals and the categorizing of the sizes of ingested meals may include analyzing blood glucose excursions in the blood glucose history. The identifying of when the user has ingested meals and the categorizing of the sizes of ingested meals may include determining when a user delivers insulin boluses and dosages of the insulin boluses. The dosages of the insulin boluses may be analyzed to categorize the sizes of the meals. The identifying of when the user has ingested meals may include determining times of meal event flags. The identifying when the user has exercised and categorizing an intensity of the identified user exercise may entail identifying when the user has activated a mode that decreases or halts automated delivery of insulin by the insulin delivery device and determining the intensity of the user exercise based on a duration that the mode remains activated.

The identifying when the user has exercised and categorizing an intensity of the identified user exercise may include analyzing the blood glucose history for an excursion to identify when the user exercised and analyzing a magnitude and/or duration of the excursion to identify the intensity of the user exercise. The identifying when the user has exercised and categorizing an intensity of the identified user exercise may entail analyzing insulin delivery history to identify when insulin delivery decreased at least a threshold amount and identifying a duration and/or magnitude of the decrease of the insulin delivery decrease to identify the intensity of the user exercise. The additional action affecting blood glucose may be one or more of the user delivering an excessive insulin bolus, the user delivering an insufficient insulin bolus, the user overestimating meal carbohydrate content, the user underestimating meal carbohydrate content, the user signaling exercise but not exercising and the user signaling a need for a correction bolus but had not ingested a meal. The cumulative response may be delivery of a specified amount of insulin to the user via the automated insulin delivery device or halting delivery of insulin to the user via the automated insulin delivery device.

Instructions for a processor to perform the method may be stored on a non-transitory computer-readable storage medium.

In accordance with an exemplary embodiment, an electronic device may include a storage medium for storing blood glucose history for a user, insulin delivery history for a user and a control software for controlling AID to the user. The electronic device may also a processor for executing the control software to perform the following. Blood glucose history, insulin bolus history and/or meal event flags for a user of the AID device are analyzed to identify when the user has ingested meals and to categorize sizes of the ingested meals. The blood glucose history, insulin delivery history and/or user-entered information for the user are analyzed to identify when the user has exercised and categorizing an intensity of the identified user exercise. The blood glucose history for the user and the insulin delivery history for the user are analyzed to determine the likelihood that the user will take additional action affecting blood glucose over time of day based on when the meals are ingested, the categorized sizes of the meals ingested, when the user exercises and the categorized intensity of exercise of the user. Fuzzy sets are established for categories of the determined likelihoods that the user will take additional action affecting blood glucose, wherein each fuzzy set is associated with a quantitative response to be taken by the AID device according to the respective categories of determined likelihoods that the user will take additional action. For a given time of day, a set membership probability is determined for each of the fuzzy sets for the user based on the determined likelihood that the user will take additional action affecting blood glucose for the given time of day. The quantitative responses of each of the fuzzy sets are weighted by the determined membership probabilities for the respective fuzzy sets. The weighted quantitative responses of the fuzzy sets are summed to determine the cumulative response to apply and the cumulative response is applied in the AID device.

BRIEF DESCRIPTION

FIG. 12 depicts an illustrative chart mapping meal and exercise parameters to likelihood categories for additional user action that affects blood glucose concentration of the user.

DETAILED DESCRIPTION

Figure 1:
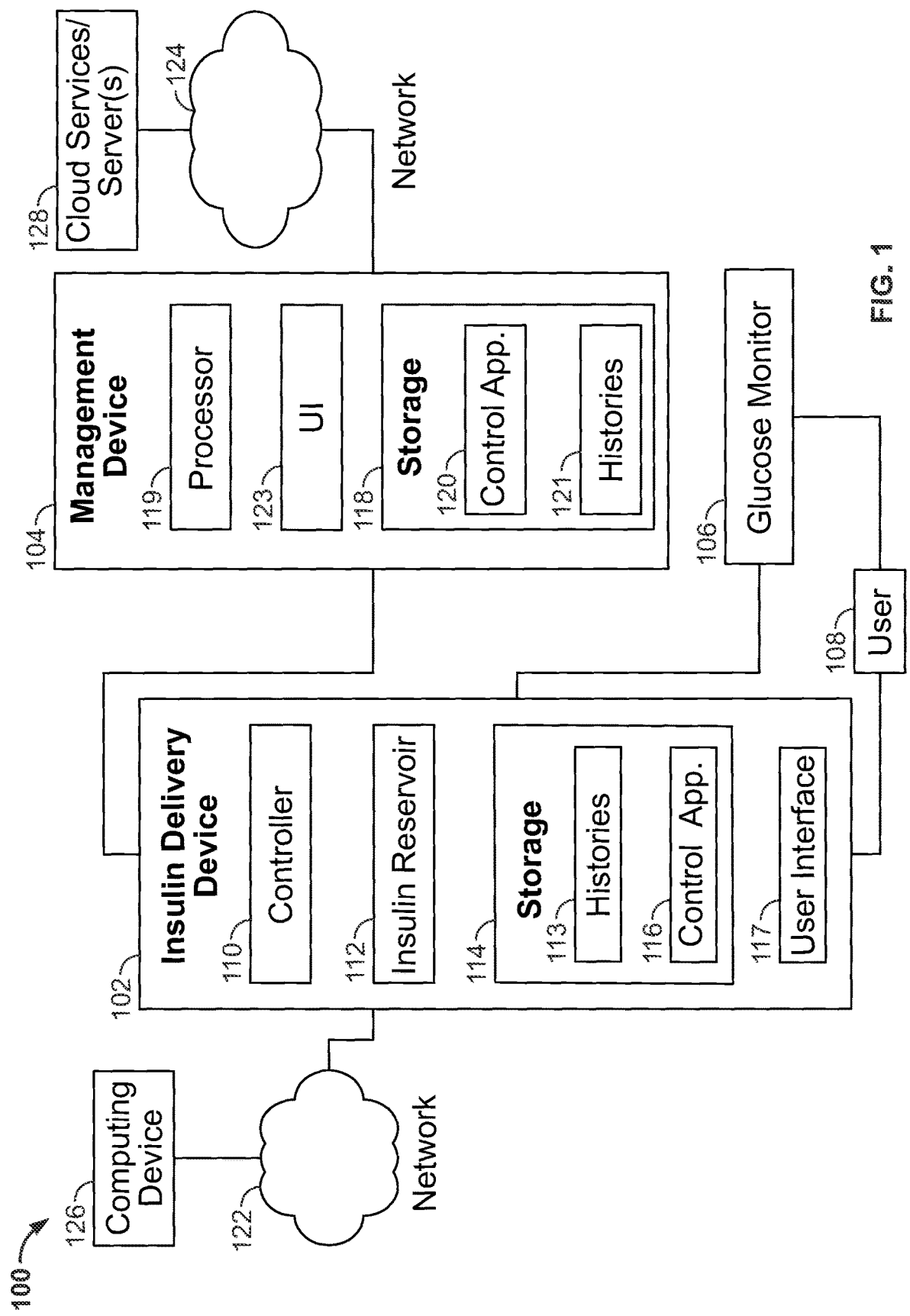
FIG. 1 depicts a block diagram of a components suitable for practicing an exemplary embodiment.

Exemplary embodiments may deploy fuzzy logic to generate a response by an AID device to possible user activity that will affect blood glucose concentration of a user based on probabilities of such user activity derived from empirical data. The problem of determining the appropriate response to the prospect of such user activity lends itself to a fuzzy logic solution rather than a binary decision solution. With the binary decision solution, the AID device would either assume that the user is taking no additional action that affects blood glucose concentration or would assume that the user is taking such additional user action. However, with the fuzzy logic solution of the exemplary embodiments, the embodiments span a broader range of cases, such as a case of low probability that the user will take additional user action, a case of a moderate probability that the user will take additional user action, a case of a high probability that the user will take additional action and a case of a very high probability of user action. The responses by the AID device to each of these cases may reflect the probability of each such case occurring as evidenced by empirical data. As such, the exemplary embodiments adopt a solution more reflective of the empirical data.

In the exemplary embodiments, a fuzzy set may be defined for each case (e.g., low, moderate, high or very high probability of the user taking additional action that affects blood glucose concentration of the user). A membership function may be provided for each fuzzy set. The membership function may provide a probability of membership in the set based on a parameter, such as time of day. Each fuzzy set may have a response that is reflective of the likelihood of additional user action associated with the fuzzy set. For example, if a user has a low probability of taking additional action that will affect blood glucose concentration of the user, as in the "low" fuzzy set, the response for the fuzzy set may be to maintain insulin delivery settings as they are. However, if there is a very high probability that the user will take additional action that will affect blood glucose concentration of the user, as in the "very high" fuzzy set, the response for the fuzzy set may be to aggressively adjust insulin delivery settings from what they are (e.g., to modify the amount of insulin delivered by a substantial amount). The cumulative response may be determined by weighting the response of each fuzzy set, such as by the probability of the associated fuzzy set and summing the weighted responses.

The probabilities provided by the membership functions may be empirically derived based on histories of the user. For instance, factors may be identified, like when a user eats a meal, the size of the meal, when a user exercises and the intensity of the exercise. Other factors may be used in alternative cases. The other factors should have a correlation to whether the user takes additional action that affects blood glucose concentration. The effect these factors have on the probability that the user will take additional action may be determined by reviewing the histories and determining the likelihood that the user will take the additional action given those factors. For example, suppose that a user took additional action 3 out of 4 times when the user exercised with a high intensity but ingested a small meal between 6 pm and 8 pm. The membership function may reflect a high probability for additional user action between 6 pm to 8 pm.

FIG. 1 depicts an illustrative drug delivery system (100) that is suitable for delivering insulin to a user (108) in an exemplary embodiment. The drug delivery system (100) includes an insulin delivery device (102). The insulin delivery device (102) may be a wearable device that is worn on the body of the user (108). The insulin delivery device (102) may be directly coupled to a user (e.g., directly attached to a body part and/or skin of the user (108) via an adhesive or the like). In an example, a surface of the insulin delivery device (102) may include an adhesive to facilitate attachment to the user (108).

The insulin delivery device (102) may include a controller (110). The controller (110) may be implemented in hardware, software, or any combination thereof. The controller (110) may, for example, be a microprocessor, a logic circuit, a field programmable gate array (FPGA), an application specific integrated circuit (ASIC) or a microcontroller coupled to a memory. The controller (110) may maintain a date and time as well as other functions (e.g., calculations or the like). The controller (110) may be operable to execute a control application (116) stored in the storage (114) that enables the controller (110) to direct operation of the insulin delivery device (102). The storage (114) may hold histories (113) for a user, such as a history of automated insulin deliveries, a history of bolus insulin deliveries, meal event history, exercise event history and the like. In addition, the controller (110) may be operable to receive data or information. The storage (114) may include both primary memory and secondary memory. The storage may include random access memory (RAM), read only memory (ROM), optical storage, magnetic storage, removable storage media, solid state storage or the like.

The insulin delivery device (102) may include an insulin reservoir (112) for storing insulin for delivery to the user (108) as warranted. A fluid path to the user (108) may be provided, and the insulin delivery device (102) may expel the insulin from the insulin reservoir (112) to deliver the insulin to the user (108) via the fluid path. The fluid path may, for example, include tubing coupling the drug delivery device (102) to the user (108) (e.g., tubing coupling a cannula to the insulin reservoir (112)).

There may be one or more communications links with one or more devices physically separated from the insulin delivery device (102) including, for example, a management device (104) of the user and/or a caregiver of the user and/or a glucose monitor (106). The communication links may include any wired or wireless communication link operating according to any known communications protocol or standard, such as Bluetooth®, Wi-Fi, a near-field communication standard, a cellular standard, or any other wireless protocol The insulin delivery device (102) may also include a user interface (117), such as an integrated display device for displaying information to the user (108) and in some embodiments, receiving information from the user (108). The user interface (117) may include a touchscreen and/or one or more input devices, such as buttons, knob or a keyboard.

The insulin delivery device (102) may interface with a network (122). The network (122) may include a local area network (LAN), a wide area network (WAN) or a combination therein. A computing device (126) may be interfaced with the network, and the computing device may communicate with the insulin delivery device (102).

The drug delivery system 100 may include a glucose monitor (106) for sensing the blood glucose concentration levels of the user (108). The glucose monitor (106) may provide periodic blood glucose concentration measurements and may be a continuous glucose monitor (CGM), or another type of device or sensor that provides blood glucose measurements. The glucose monitor (106) may be physically separate from the insulin delivery device (102) or may be an integrated component thereof. The glucose monitor (106) may provide the controller (110) with data indicative of measured or detected blood glucose levels of the user (108). The glucose monitor (106) may be coupled to the user (108) by, for example, adhesive or the like and may provide information or data on one or more medical conditions and/or physical attributes of the user (108). The information or data provided by the glucose monitor (106) may be used to adjust drug delivery operations of the insulin delivery device (102).

The drug delivery system (100) may also include the management device (104). The management device (104) may be a special purpose device, such as a dedicated personal diabetes manager (PDM) device. The management device (104) may be a programmed general purpose device, such as any portable electronic device including, for example, a dedicated controller, such as processor, a smartphone, or a tablet. The management device (104) may be used to program or adjust operation of the drug delivery device (102) and/or the sensor (104). The management device (104) may be any portable electronic device including, for example, a dedicated controller, a smartphone, or a tablet. In the depicted example, the management device (104) may include a processor (119) and a storage (118). The processor (119) may execute processes to manage a user's blood glucose levels and for control the delivery of the drug or therapeutic agent to the user (108). The processor (119) may also be operable to execute programming code stored in the storage (118). For example, the storage may be operable to store one or more control applications (120) for execution by the processor (119). The storage (118) may store the control application (120), histories (121) like those described above for the insulin delivery device (102) and other data and/or programs.

The management device (104) may include a user interface (123) for communicating with the user (108). The user interface may include a display, such as a touchscreen, for displaying information. The touchscreen may also be used to receive input when it is a touch screen. The user interface (123) may also include input elements, such as a keyboard, button, knobs or the like.

The management device 104 may interface with a network (124), such as a LAN or WAN or combination of such networks. The management device (104) may communicate over network (124) with one or more servers or cloud services (128). The role that the one or more servers or cloud services (128) may play in the exemplary embodiments will be described in more detail below.

Figure 2:
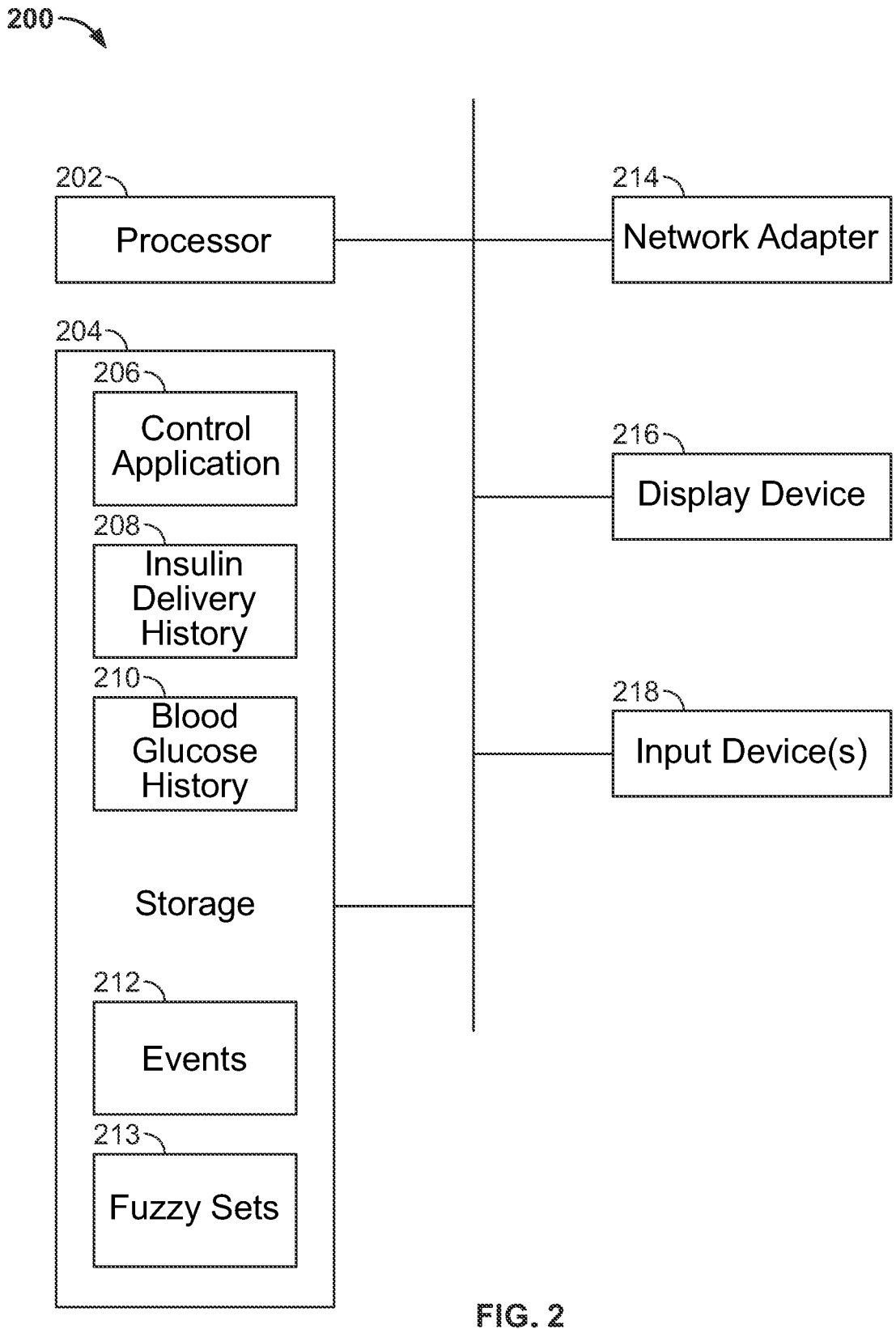
FIG. 2 depicts a block diagram of a device suitable for controlling insulin delivery in by an insulin delivery device.

FIG. 2 depicts a block diagram of a device (200) suitable for performing the methods that will be described in more detail below. The device (200) may in different exemplary embodiments be the insulin delivery device (102), the management device (104), the computing device (126) or the one or more servers (128). Where the device is the computing device (126), or the one more servers or cloud services (128), the device (200) may act in cooperation with the management device (104) and the insulin delivery device (102) to perform the methods. The device (200) includes a processor (202) for executing programming instructions. The processor (202) has access to a storage (204). The storage (204) may store an application (206) for performing the methods. This application (206) may be executed by the processor (202). The storage (204) may store an insulin delivery history (208) for the user. The insulin delivery history (208) may contain data regarding the amount of insulin delivered as well as the date and time of the deliveries. The insulin delivery history (208) may also identify if each delivery is a basal delivery or a bolus delivery. The storage (204) may store the blood glucose history (210). The blood glucose history (210) may include blood glucose concentration readings as well as the date and time of such readings. These values may be obtained by the glucose monitor (106). The storage (204) additionally may store information regarding events (212), like meal events and exercise events. The storage may hold information regarding the fuzzy sets (213), including their associated member functions.

The device (200) may include a network adapter (214) for interfacing with networks, like networks (122 and 124). The device (200) may have a display device (216) for displaying video information. The display device (216) may be, for instance, a liquid crystal display (LCD) device, a light emitting diode (LED) device, etc. The device (200) may include one or more input devices (218) for enabling input to be received. Examples of input devices include keyboards, mice, pointing devices, touchscreen displays, button, knobs or the like.

Figure 3:
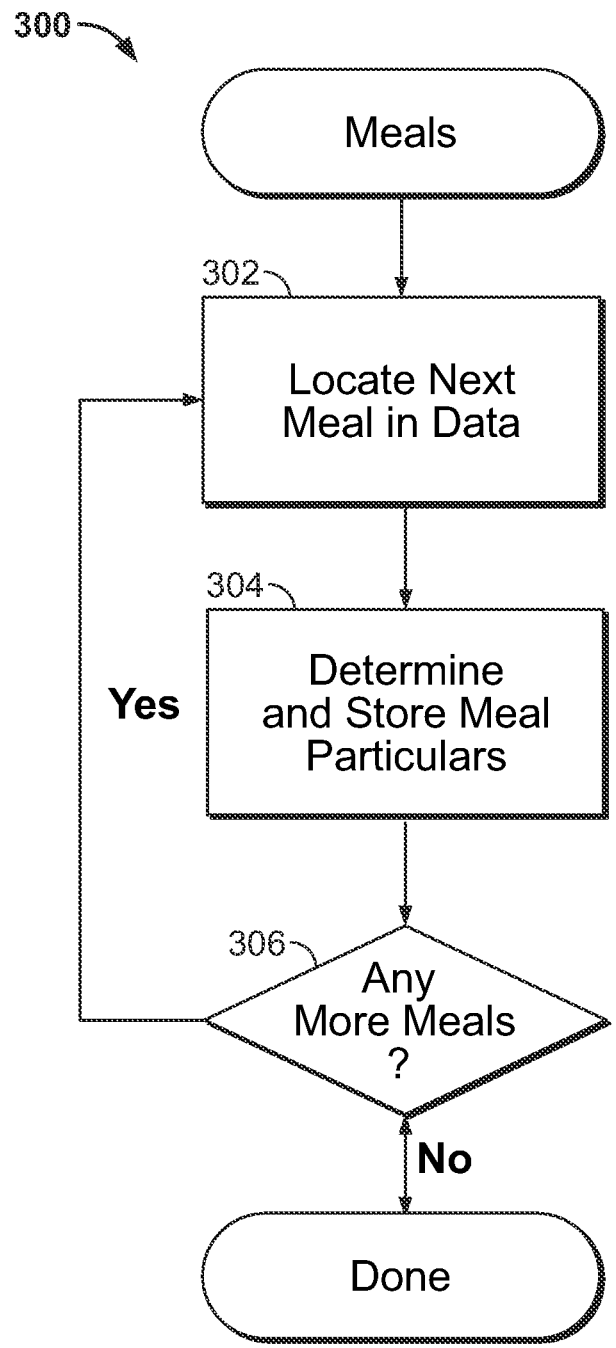
FIG. 3 depicts a flowchart illustrating steps that may be performed to locate meals in historical data for a user.

As was mentioned above, the exemplary embodiments may analyze empirical data for the user to identify instances where the user partakes in meals and to determine information regarding such meals. Initially, information regarding the meals must be identified in the empirical data. For example, the empirical data may be analyzed to identify when meals occur and the size of each meal. Thus, as shown in the flowchart (300) of FIG. 3, the exemplary embodiments may analyze the empirical data to locate a next meal (302). The empirical data may hold data for multiple, days, weeks or months. The data is analyzed in sequential fashion from a start date/time to an end date/time. Once the next meal is located, the particulars regarding the meal may be determined and stored in a storage (304), such as storage (204). A check is made whether there are indicators of a next meal in the empirical data (306). If so, the process is repeated beginning with (302). Otherwise the process is completed for meals in the empirical data.

Figure 4:
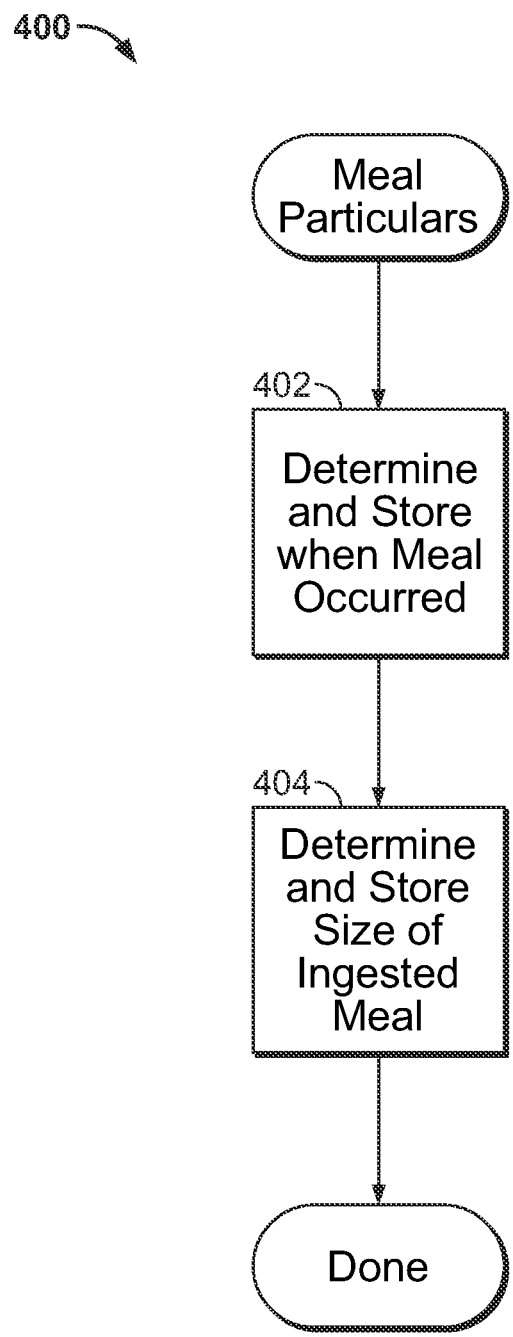
FIG. 4 depicts a flowchart illustrating steps that may be performed in determining the particulars of meals.

FIG. 4 shows a flowchart (400) of steps that may be performed in identifying and storing meal particulars (304). The process may determine and store information regarding when a meal occurs (402). This may include, for example, date, time and/or duration information for the meal. How the meal is identified may depend on the nature of the empirical data, as will explained below relative to examples with different types of empirical data. The determining of the meal particulars may also include identifying the size of the meal ingested or alternatively determining the amount of carbohydrates ingested (404). In general, the size of the meal is a sufficient proxy for the amount of carbohydrates ingested. Such information may be stored for future reference.

Figure 5:
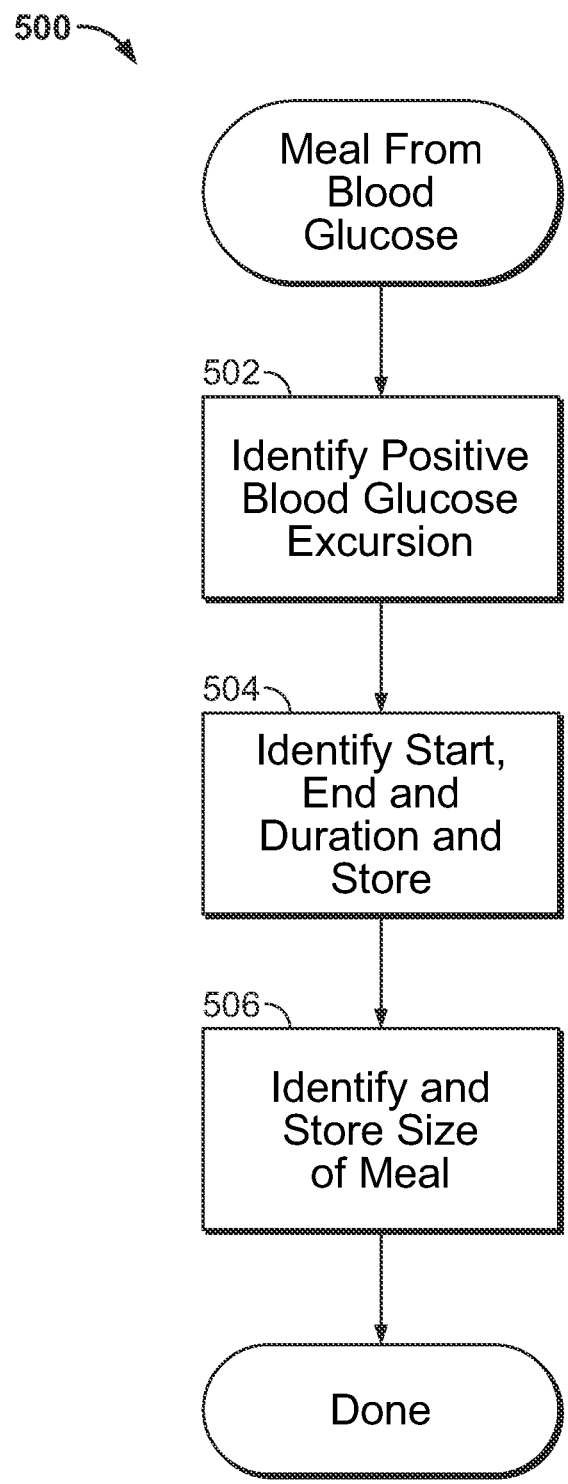
FIG. 5 depicts a flowchart of steps that may be performed to identify meals and meal particulars from user blood glucose history.

One type of empirical data may be blood glucose concentration history for a user. FIG. 5 shows a flowchart (500) for the steps that may be performed to identify meal information when the empirical data is blood glucose concentration history. In looking for meals, the process may look for positive blood glucose excursions in the blood glucose concentration history. Since ingesting a meal increases the blood glucose concentration of the user, this should be reflected in the blood glucose concentration history of the user as a positive excursion. Hence, the process identifies positive blood glucose excursions in the blood glucose concentration history (502). The start and end of the excursion may be noted to determine the start time, end time and duration of the excursion (504). Once the blood glucose excursion is noted, the process may work backwards to figure out the time when the meal was ingested based on the typical delay before the meal is reflected in the blood glucose history. Alternatively, the time which the blood glucose concentration increase begins may be noted and used by the process to identify when the meal that was ingested appears in the blood glucose concentration history. The process also identifies the size of the meal ingested (506). The magnitude of the increase in blood concentration during the excursion may reflect the size of the meal ingested. More particularly, the process is interested in the amount of carbohydrates ingested, which is generally reflected in the size of the meal ingested. The duration of the blood glucose excursion may also be used as an indicator of the size of the meal ingested. This is because a bigger meal will result in a longer blood glucose excursion than a smaller meal.

Figure 6:
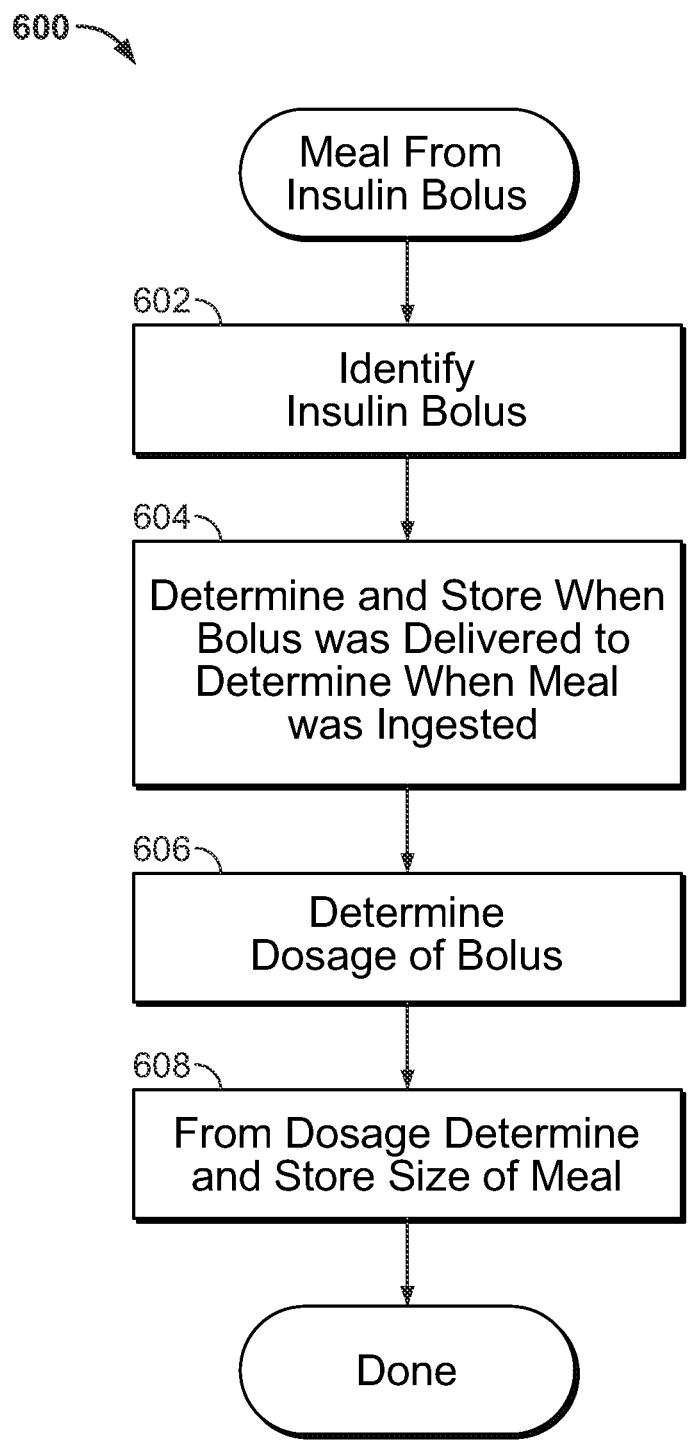
FIG. 6 depicts a flowchart of steps that may be performed to identify meals and meal particulars from insulin boluses.

The empirical data may be the insulin bolus delivery history for the user. The history of insulin bolus deliveries may be analyzed to determine when meals are ingested and the size of meals. FIG. 6 depicts a flowchart (600) depicting steps that may be performed in analyzing the history of insulin bolus deliveries to the user. First, the process begins by identifying an insulin bolus delivery to the user in the history being analyzed (602). If the history includes all insulin deliveries to the user, the boluses may be identified by their magnitude as they are larger in dose than basal insulin deliveries from the AID device. The time of the insulin bolus delivery is identified (604). The time may reflect the time of day alone or a combination of date and time or day of the week and time. The dosage of the bolus that was delivered is determined (606), and the dosage is used as to estimate the size of the meal ingested (608). Generally, a user chooses a dosage for an insulin bolus that matches the size of meal they ingest. This assumes that the user delivers a bolus of the correct amount.

Figure 7:
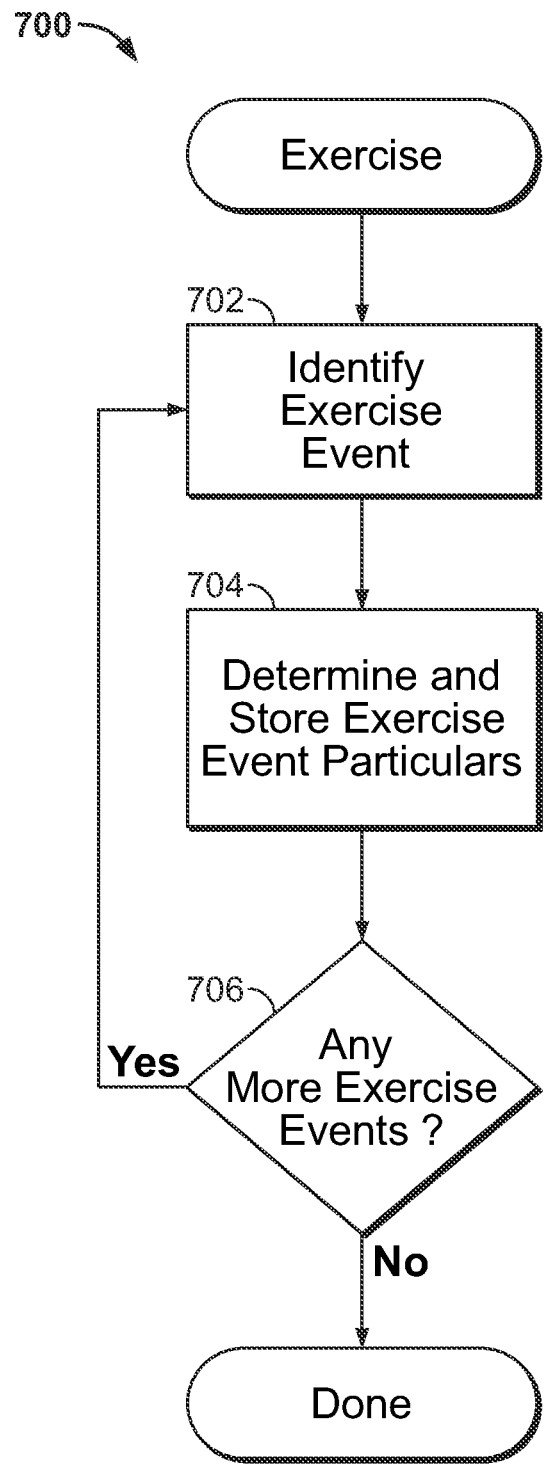
FIG. 7 depicts a flowchart illustrating steps that may be performed to locate exercise by a user in historical data for the user.

As was mentioned above, other factors correlated to whether a user takes additional action that affects blood glucose concentration, such as user exercise and the intensity of the user exercise, may be located and noted in the empirical data. FIG. 7 depicts a flowchart (700) of steps that may be performed by exemplary embodiments to identify information regarding user exercise in the empirical data. First, an exercise event is identified in the empirical data (702). The particulars of the exercise event are determined and stored (704). Analysis of the empirical data continues by checking if there is another exercise event indicated by the empirical data (706). If not, the process is complete. If so, the process repeats for the next exercise event beginning at (702).

Figure 8:
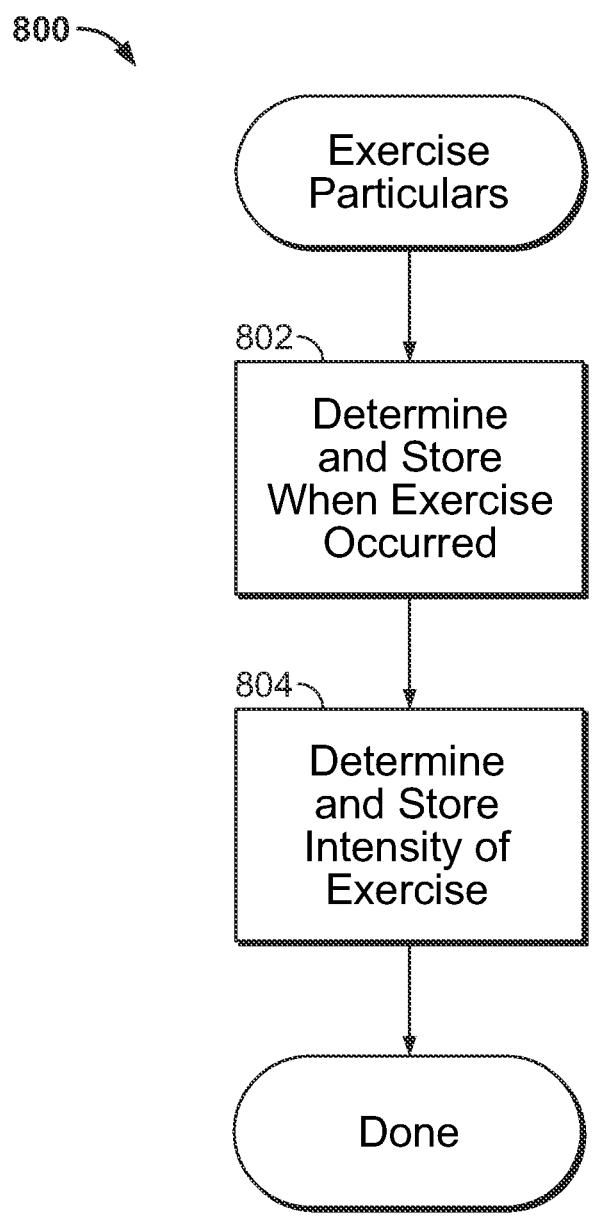
FIG. 8 depicts a flowchart illustrating steps that may be performed in determining the particulars of user exercise.

FIG. 8 depicts a flowchart (800) depicting more detail regarding the particulars that are determined and stored for the exercise event (see 704). A determination is made from the empirical data when the exercise event began is stored (802). The intensity of the exercise is also determined and stored (804).

Figure 9:
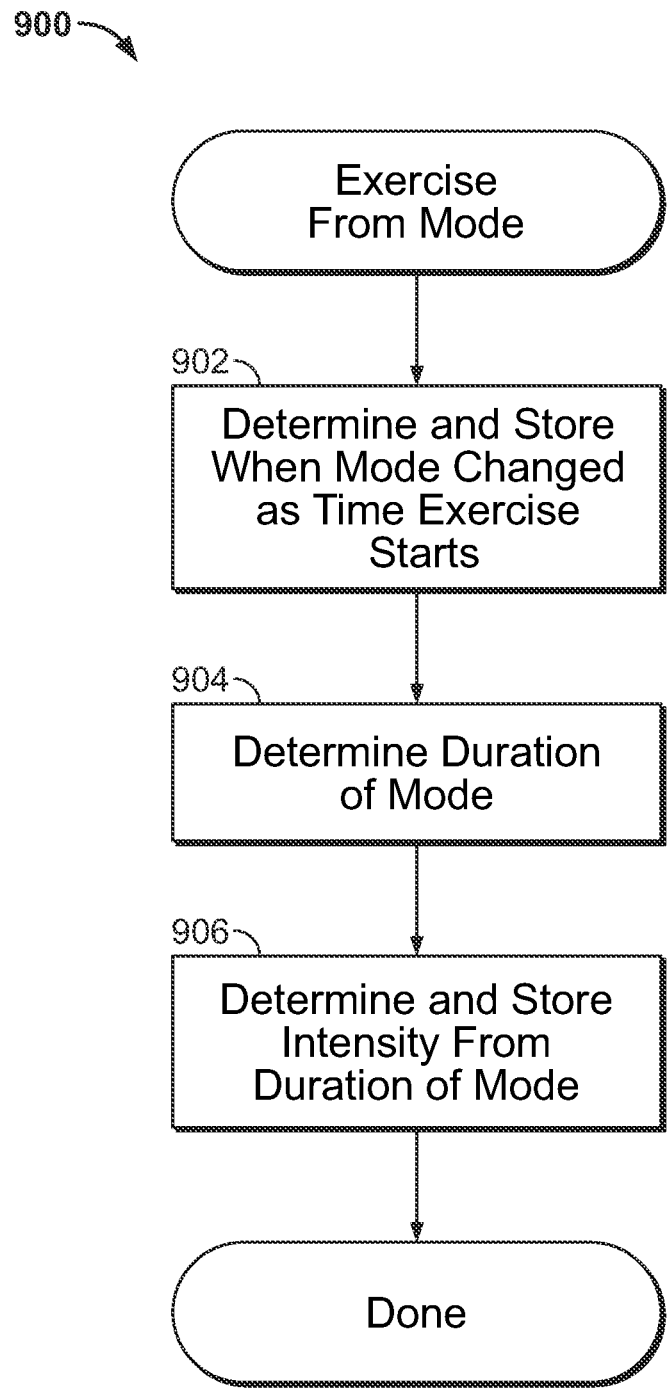
FIG. 9 depicts a flowchart of steps that may be performed to identify user exercise and user exercise particulars from mode information.

Some AID devices have a mode to indicate exercise or to protect against hypoglycemia. The history of when this mode is invoked and how long the remains active may be analyzed to identify exercise events and the intensity of the exercise. FIG. 9 depicts a flowchart (900) illustrating how such mode information may be analyzed. First, when the mode changes may be determined to be when the exercise event begins (902) and may be stored. This may be recorded as time and optionally date information. The duration over which the mode is active may be determined from the empirical data (904). The intensity of the exercise event may be determined from the duration over which the mode is active and stored (906). The duration roughly equates with how long the user exercises and hence is reflective of the intensity of the exercise.

Figure 10:
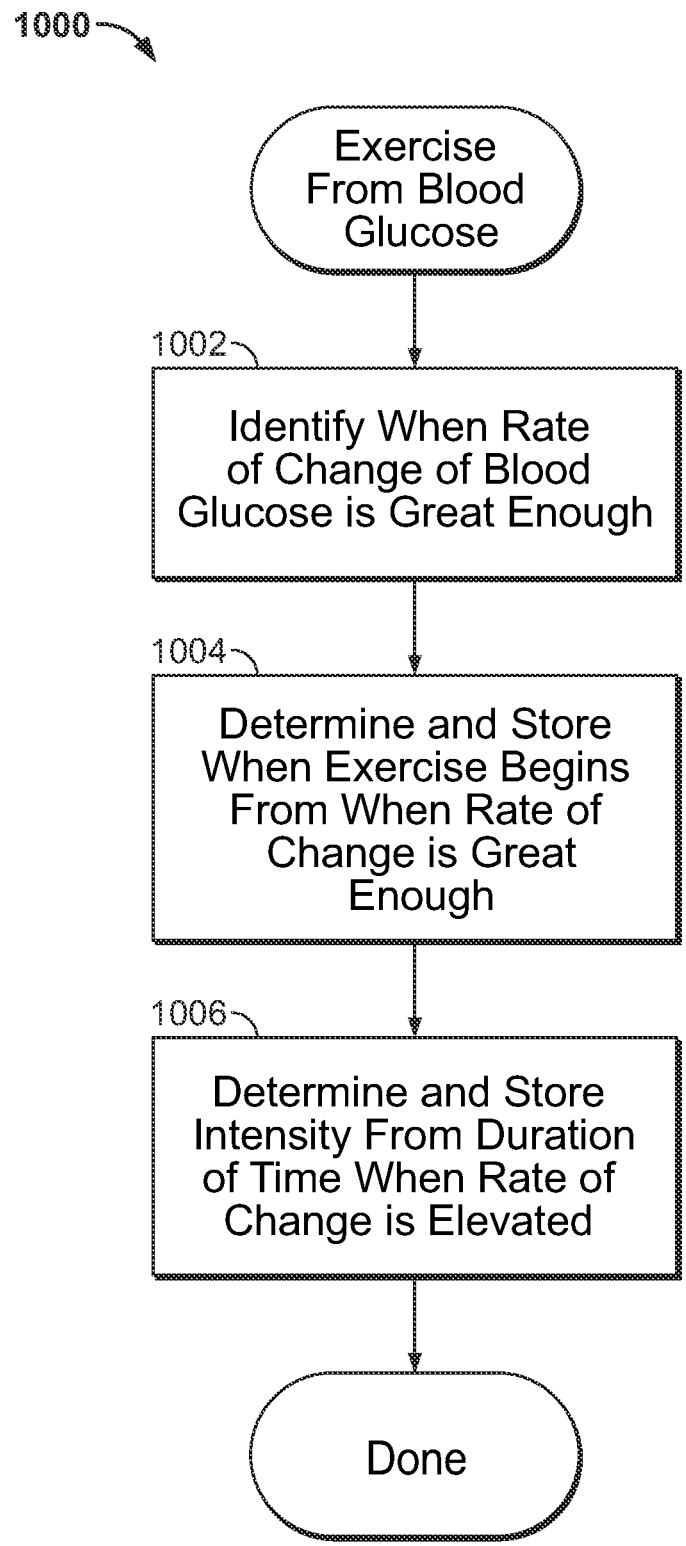
FIG. 10 depicts a flowchart of steps that may be performed to identify user exercise and user exercise particulars from blood glucose information.

The exercise event information may also be identified in empirical data in the form of blood glucose concentration history. FIG. 10 depicts a flowchart (1000) of steps that may be performed to identify exercise event information from blood glucose concentration history for a user. Initially, a determination is made of when the rate of decrease is blood glucose concentration is great enough to indicate an exercise event (1002). When the rate of change in the decrease in blood glucose concentration is great enough, it is an indication of when the user began exercising and is stored (1004). The intensity of the exercise may then be determined and stored (1006). The duration of time over which the rate of decrease in blood glucose concentration is elevated may be used to determine how long the user exercised and thus, may be used to determine the intensity of user exercise and is stored (1008).

Figure 11:
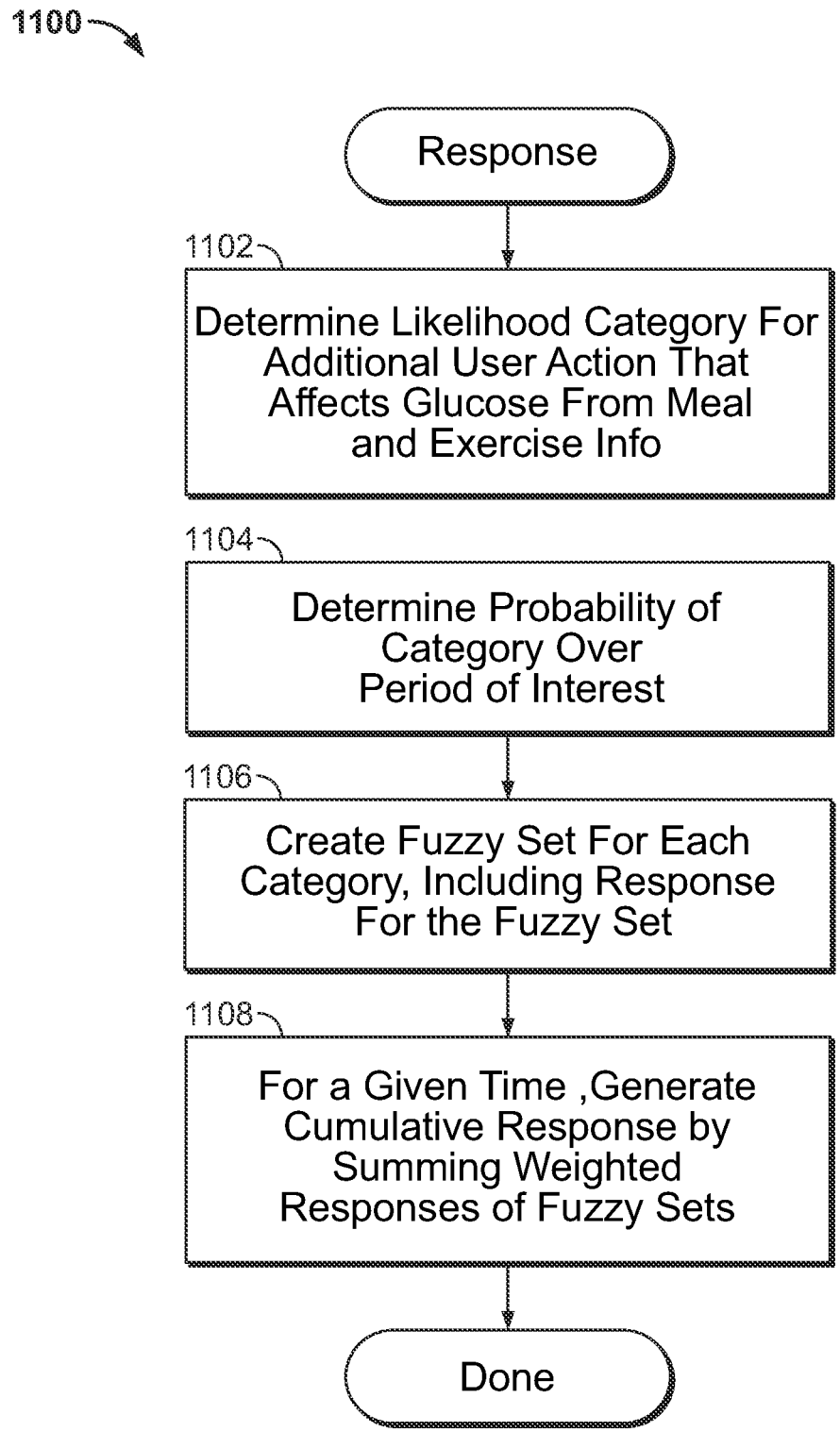
FIG. 11 depicts a flowchart of steps that may be performed to identify a response derived from using fuzzy sets.

Once the meal particulars and the exercise particulars have been identified in the empirical data, the meal particulars and the exercise particulars may be used as depicted in the flowchart (1100) of FIG. 11. Specifically, as was discussed above, the empirical data is processed to identify the likelihood that meal events and exercise events may lead to additional action by the user that affects blood glucose concentrations by the user (1102). Thus, the analysis looks at when meals are ingested and the size of the meals as well as when a user exercises and the intensity of the exercise to determine a correlation to the user taking additional action that affects blood glucose concentration. FIG. 12 depicts an illustrative table 1200 that shows the correlation. The columns (1202) each reflect an intensity level of user exercise and the rows (1204) reflect a size of meal for the user (relative to a normal size meal). There is a row (1206) for a low sized meal, a row (1208) for a normal sized meal and a row (1210) for a high sized meal. There are columns for no exercise (1212), a column for low intensity exercise (1214), a column for medium intensity exercise (1216) and a column for high intensity exercise (1218).

Each entry reflects a likelihood that the user will take additional action which will affect blood glucose concentration based on the size of meal ingested and the intensity of user exercise. The empirical data is analyzed to determine these likelihood categories. In the illustrative table (1200), the empirical data indicates there is a low likelihood of the user taking additional action that affects blood glucose concentration if the user eats a normal size meal and does not exercise as reflected by entry (1220). However, there is a moderate probability of the user taking additional action that affects blood glucose concentration if the user eats a normal sized meal and exercises with a low intensity as indicated by entry (1222). The likelihood increases to a high probability if the user eats a high sized meal and exercises with a low intensity as indicated by entry (1224). The likelihood increases to a very high probability if the user eats a high sized meal and exercises with a high intensity as indicated by entry (1226).

Figure 13:
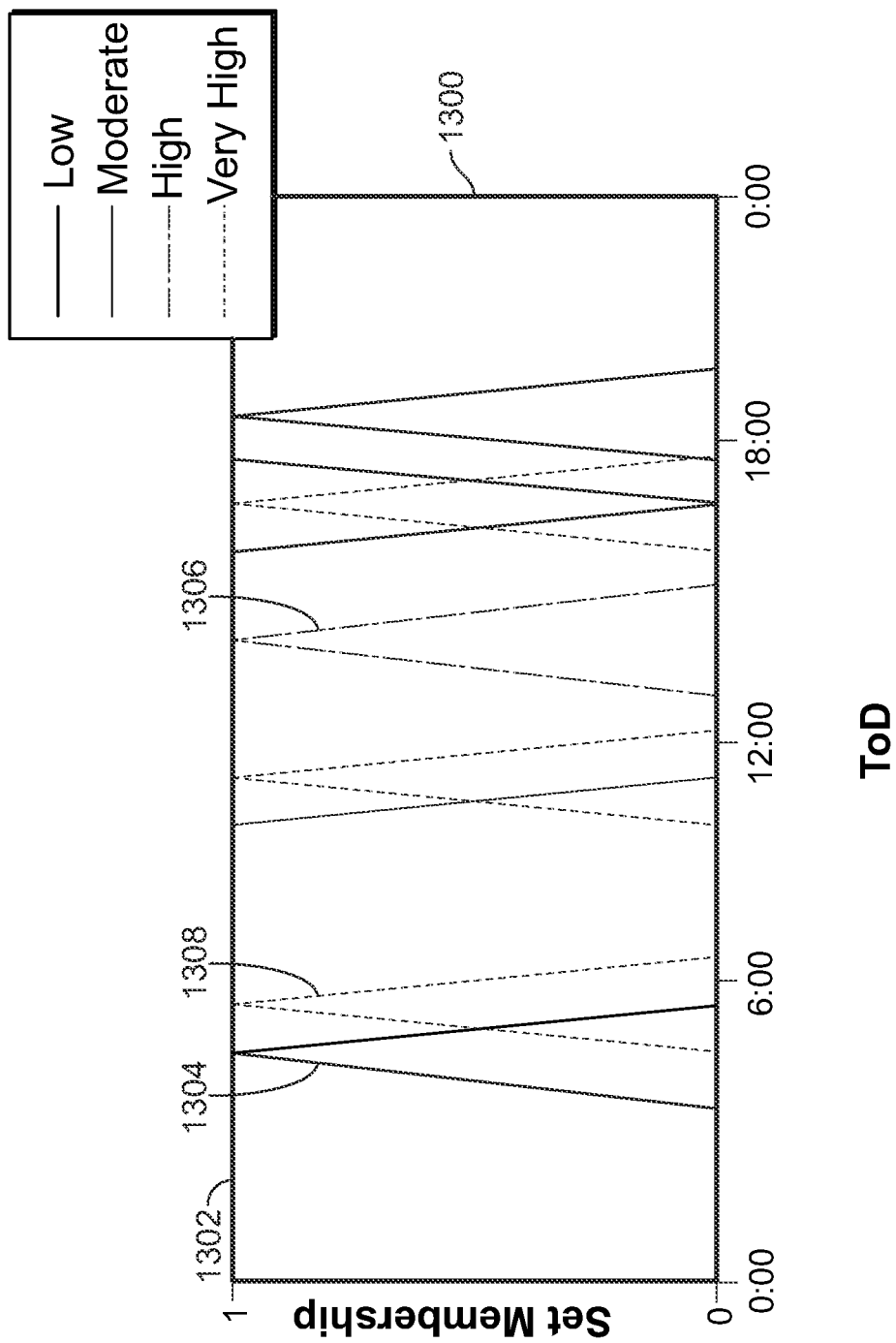
FIG. 13 depicts an illustration of a plot of probabilities of exemplary fuzzy sets over time of day.

The probability of such categories of likelihood are determined over time (a period of interest) (1104). This may entail determining how often each of the meal size/exercise intensity pairs of the table occur and what category is associated with the pair. For example, the probability of the moderate category can be determined by adding the probability for the entries having that category as a value (i.e., the probability of the high meal size and no exercise and the probability of the normal meal size and low intensity exercise). FIG. 13 depicts a plot (1300) of probability curves for the low likelihood category (1302), the moderate likelihood category (1304), the high likelihood category (1306) and the very high likelihood category (1308). As can be seen, each curve contains probability values ranging from 0 to 1 that vary over time of day beginning at midnight and extending for 24 hours.

Those skilled in the art will appreciate that the period of time for the probabilities need not be hours and may extend beyond a single day to multiple days or weeks. Moreover, different number of likelihood categories may be used and different correlated factors may be used.

Fuzzy sets are created for each of the categories (1106). Each of the categories has a response for the insulin delivery settings that is reflective of the associated likelihood that the user will take additional action that affects blood glucose concentration. These settings may reflect parameters, such as constraints that may be loosened or tightened. Each fuzzy set has a membership function reflective of the probability of the likelihood category over time of day (as reflected by the curves (1302), (1304), (1306) and (1308) in FIG. 13).

For any given point at time, the control application may use membership function for each likelihood category to obtain a probability of that category. The response of each category may be weighted, such as by the probability provided by the associate membership function, and the cumulative response may be determined to the sum of the category response weighted by their respective probabilities (1108). For example, given respective probabilities of 0.5, 0.25, 0.25 and 0 for the fuzzy sets, the cumulative response could be determined as:

Cumulative response=0.5*response of the low fuzzy set+0.25*the response of moderate fuzzy set+ 0.25*the response of high fuzzy set+0.0*the response of the very high fuzzy set.

The weights also may include weighting coefficients and offsets in addition to the probability value.

While the present invention has been described herein relative to exemplary embodiments, those skilled in the art will appreciate that various changes in form and detail may be made without departing from the intended scope as defined by the appended claims.

The invention claimed is:

1. A method performed by a processor for controlling an automated insulin delivery device, comprising:
   analyzing blood glucose history, insulin bolus history and/or meal event flags for a user of the automated insulin delivery device to identify when the user has ingested meals and to categorize sizes of the ingested meals;
   analyzing the blood glucose history, insulin delivery history and/or user-entered information for the user to identify when the user has exercised and categorizing an intensity of the identified user exercise;
   determining likelihood categories for additional user action affecting blood glucose based on when the meals are ingested, the categorized sizes of the meals ingested, when the user exercises and the categorized intensity of exercise of the user, each likelihood category representing a range of probabilities that the user will take additional action;
   creating a fuzzy set for each of the categories, wherein each fuzzy set is associated with a quantitative response to be taken by the automated insulin delivery device according to the respective categories of determined likelihoods that the user will take additional action affecting blood glucose;
   for a given time of day, determining a set membership probability for each of the fuzzy sets for the user;
   weighting the quantitative responses of each of the fuzzy sets by the determined membership probabilities for the respective fuzzy sets for the given time of day;
   summing the weighted quantitative responses of the fuzzy sets to determine the cumulative response to apply for the given time of day; and
   applying the cumulative response in the automated insulin delivery device.

2. The method of claim 1, wherein the identifying of when the user has ingested meals and the categorizing of the sizes of ingested meals comprises analyzing blood glucose excursions in the blood glucose history.

3. The method of claim 1, wherein the identifying of when the user has ingested meals and the categorizing of the sizes of ingested meals comprises determining when a user delivers insulin boluses and dosages of the insulin boluses.

4. The method of claim 3, wherein the dosages of the insulin boluses are analyzed to categorize the sizes of the meals.

5. The method of claim 1, wherein the identifying of when the user has ingested meals comprises determining times of meal event flags.

6. The method of claim 1, wherein the identifying when the user has exercised and categorizing an intensity of the identified user exercise comprises identifying when the user has activated a mode that decreases or halts automated delivery of insulin by the insulin delivery device and determining the intensity of the user exercise based on a duration that the mode remains activated.

7. The method of claim 1, wherein the identifying when the user has exercised and categorizing an intensity of the identified user exercise comprises analyzing the blood glucose history for an excursion to identify when the user exercised and analyzing a magnitude and/or duration of the excursion to identify the intensity of the user exercise.

8. The method of claim 1, wherein the identifying when the user has exercised and categorizing an intensity of the identified user exercise comprises analyzing insulin delivery history to identify when insulin delivery decreased at least a threshold amount and identifying a duration and/or magnitude of the decrease of the insulin delivery decrease to identify the intensity of the user exercise.

9. The method of claim 1, wherein the additional action affecting blood glucose is one or more of the user delivering an excessive insulin bolus, the user delivering an insufficient insulin bolus, the user overestimating meal carbohydrate content, the user underestimating meal carbohydrate content, the user signaling exercise but not exercising and the user signaling a need for a correction bolus but had not ingested a meal.

10. The method of claim 1, wherein the cumulative response is delivery of a specified amount of insulin to the user via the automated insulin delivery device or halting delivery of insulin to the user via the automated insulin delivery device.

11. A non-transitory computer-readable storage medium storing instructions that cause a processor to:
analyze blood glucose history, insulin bolus history and/or meal event flags for a user of the automated insulin delivery device to identify when the user has ingested meals and to categorize sizes of the ingested meals;
analyze the blood glucose history, insulin delivery history and/or user-entered information for the user to identify when the user has exercised and categorizing an intensity of the identified user exercise;
determine likelihood categories for additional user action affecting blood glucose based on when the meals are ingested, the categorized sizes of the meals ingested, when the user exercises and the categorized intensity of exercise of the user, each likelihood category representing a range of probabilities that the user will take additional action;
create a fuzzy set for each of the categories, wherein each fuzzy set is associated with a quantitative response to be taken by the automated insulin delivery device according to the respective categories of determined likelihoods that the user will take additional action affecting blood glucose;
for a given time of day, determine a set membership probability of each of the fuzzy sets for the user;
weight the quantitative responses of each of the fuzzy sets by the determined membership probabilities for the respective fuzzy sets for the given time of day;
sum the weighted quantitative responses of the fuzzy sets to determine the cumulative response to apply for the given time of day; and
apply the cumulative response in the automated insulin delivery device.

12. The non-transitory computer-readable storage medium of claim 11, wherein the identifying of when the user has ingested meals and the categorizing of the sizes of ingested meals comprises analyzing blood glucose excursions in the blood glucose history.

13. The non-transitory computer-readable storage medium of claim 11, wherein the identifying of when the user has ingested meals and the categorizing of the sizes of ingested meals comprises determining when a user delivers insulin boluses and dosages of the insulin boluses.

14. The non-transitory computer-readable storage medium of claim 13, wherein the dosages of the insulin boluses are analyzed to categorize the sizes of the meals.

15. The non-transitory computer-readable storage medium of claim 11, wherein the identifying of when the user has ingested meals comprises determining times of meal event flags.

16. The non-transitory computer-readable storage medium of claim 11, wherein the identifying when the user has exercised and categorizing an intensity of the identified user exercise comprises identifying when the user has activated a mode that decreases or halts automated delivery of insulin by the insulin delivery device and determining the intensity of the user exercise based on a duration that the mode remains activated.

17. The non-transitory computer-readable storage medium of claim 11, wherein the identifying when the user has exercised and categorizing an intensity of the identified user exercise comprises analyzing the blood glucose history for an excursion to identify when the user exercised and analyzing a magnitude and/or duration of the excursion to identify the intensity of the user exercise.

18. The non-transitory computer-readable storage medium of claim 11, wherein the identifying when the user has exercised and categorizing an intensity of the identified user exercise comprises analyzing insulin delivery history to identify when insulin delivery decreased at least a threshold amount and identifying a duration and/or magnitude of the decrease of the insulin delivery decrease to identify the intensity of the user exercise.

19. The non-transitory computer-readable storage medium of claim 11, wherein the additional action affecting blood glucose is one or more of the user delivering an excessive insulin bolus, the user delivering an insufficient insulin bolus, the user overestimating meal carbohydrate content, the user underestimating meal carbohydrate content, the user signaling exercise but not exercising and the user signaling a need for a correction bolus but had not ingested a meal.

20. The non-transitory computer-readable storage medium of claim 11, wherein the cumulative response is one of delivery of a specified amount of insulin to the user via the automated insulin delivery device or halting delivery of insulin to the user via the automated insulin delivery device.

21. An electronic device comprising:
a storage medium for storing blood glucose history for a user, insulin delivery history for a user and a control software for controlling automated insulin delivery to the user; and
a processor for executing the control software for:
analyzing blood glucose history, insulin bolus history and/or meal event flags for a user of the automated insulin delivery device to identify when the user has ingested meals and to categorize sizes of the ingested meals;

analyzing the blood glucose history, insulin delivery history and/or user-entered information for the user to identify when the user has exercised and categorizing an intensity of the identified user exercise;

determining likelihood categories for additional user action affecting blood glucose based on when the meals are ingested, the categorized sizes of the meals ingested, when the user exercises and the categorized intensity of exercise of the user, each likelihood category representing a range of probabilities that the user will take additional action affecting blood glucose;

creating a fuzzy set for each of the likelihood categories wherein each fuzzy set is associated with a quantitative response to be taken by the automated insulin delivery device according to the respective categories of determined likelihoods that the user will take additional action affecting blood glucose;

for a given time of day, determining a set membership probability for each of the fuzzy sets for the user;

weighting the quantitative responses of each of the fuzzy sets by the determined membership probabilities for the respective fuzzy sets for the given time of day;

summing the weighted quantitative responses of the fuzzy sets to determine the cumulative response to apply for the given time of day; and applying the cumulative response in the automated insulin delivery device.

* * * * *